United States Patent [19]
Healy

[11] 4,380,999
[45] Apr. 26, 1983

[54] STEPPED SURGICAL RETRACTOR

[76] Inventor: Keelin E. Healy, 3402 Treehouse Pkwy., Norcross, Ga. 30093

[21] Appl. No.: 169,022

[22] Filed: Jul. 15, 1980

[51] Int. Cl.³ .............................................. A61B 17/02
[52] U.S. Cl. .......................................... 128/20; 128/3; 248/297.3
[58] Field of Search ...................... 128/3, 20; 433/138; 248/507, 297.3, 210, 211, 238

[56] References Cited
U.S. PATENT DOCUMENTS

| | | | |
|---|---|---|---|
| 1,017,174 | 2/1912 | Sander et al. | 248/297.3 |
| 2,670,732 | 3/1954 | Nelson | 128/20 |
| 2,984,446 | 5/1961 | Richter | 248/238 |
| 3,394,700 | 7/1968 | Yamamoto | 128/20 |
| 3,884,078 | 5/1968 | Gauthier | 128/20 |
| 4,155,355 | 5/1979 | Yamamoto | 128/20 |

Primary Examiner—Richard J. Apley
Assistant Examiner—J. L. Kruter
Attorney, Agent, or Firm—Patrick F. Henry

[57] ABSTRACT

A surgical retractor particularly for retracting an internal organ such as the liver during surgery. A ladder-like support is designed to fit a universal clamp on the operating table and a rigid elongated strip of material is positioned over a selected one of the ladder rungs. The strip comprises a plurality of spaced hooks which hook over a respective rung and the retractor end of the strip is curved to fit around an organ such as the liver. In operation, the particular height rung is selected for height and the strip is positioned to hook onto the rung depending upon the selected length of the strip desired with respect to the patient. Adjustment may be effected quickly and easily during surgery.

7 Claims, 2 Drawing Figures

STEPPED SURGICAL RETRACTOR

BACKGROUND OF THE INVENTION

1. Field of the Invention

Medicine and surgery and particularly surgical instruments and devices such as retractors.

2. Description of the Prior Art

In U.S. Pat. Nos. 2,670,732; 3,196,865; 3,542,015; 3,858,578 and 4,143,652 there are shown various types of instruments and devices which may be used as retractors during surgery. Each of the above-noted retractors includes some sort of means clamped to a fixed support, such as the operating table. However, none of these devices are suitable for use to retract certain organs such as the liver if for no other reason due to the difficulty in assembling, adjusting and positioning the retracting portion of the retractor. In the past it has been necessary for a nurse or other attendant to hold a liver manually out of place during the entire time that the surgeon is working which might be several hours. This can be physically exhausting. Those prior patented devices which are primarily used for holding wounds or incisions open during surgery are not suitable for use for holding a liver out of position because the sharp edges could lacerate the liver. The present method and retractor device is suitable for retracting the liver during surgery.

SUMMARY OF THE INVENTION

A surgical retractor particularly suitable for retracting a liver during surgery comprises an upwardly extending support member for attachment to a stationary surface such as the operating table and a plurality of positions on said member spaced upwardly from each other, a rigid liver retracting strip having a plurality of positions thereon selectively engageable with the positions on said upstanding member, and a curved liver retracting end portion on said strip for engagement with the liver.

A primary purpose of the present invention is to provide a surgical retractor which is easy to install on the operating table and quickly adjusted from one position to another.

Another object of this invention resides in the simplicity of construction wherein the support member is a ladder-like device with spaced members similar to the rungs on a ladder providing a plurality of selected positions for height, and a liver retracting strip having a plurality of hooks which selectively hook in one of the support members.

An additional object of this invention is found in the simplicity of construction which makes the device economical to manufacture and purchase for an operating room.

Another object of the present invention resides in the simplicity of construction whereby the device may be easily cleaned, autoclaved or otherwise sterilized.

Other and further objects and advantages of this invention will become apparent upon reading the following description of a preferred embodiment taken in conjunction with the accompanying drawings.

DESCRIPTION OF A PREFERRED EMBODIMENT

Figure 1:
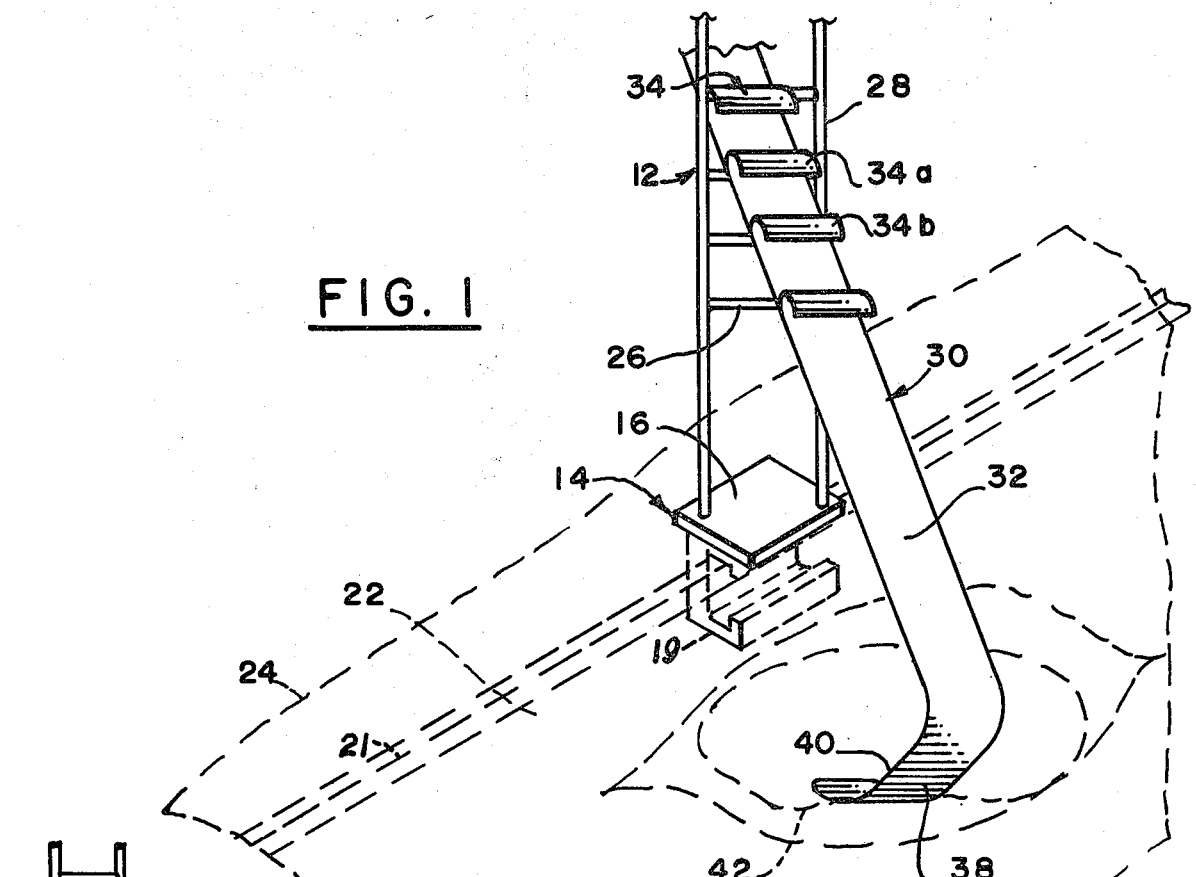
FIG. 1 is a perspective view of the present device shown holding back and retracting the liver on a patient illustrated in dotted lines.
Figure 2:
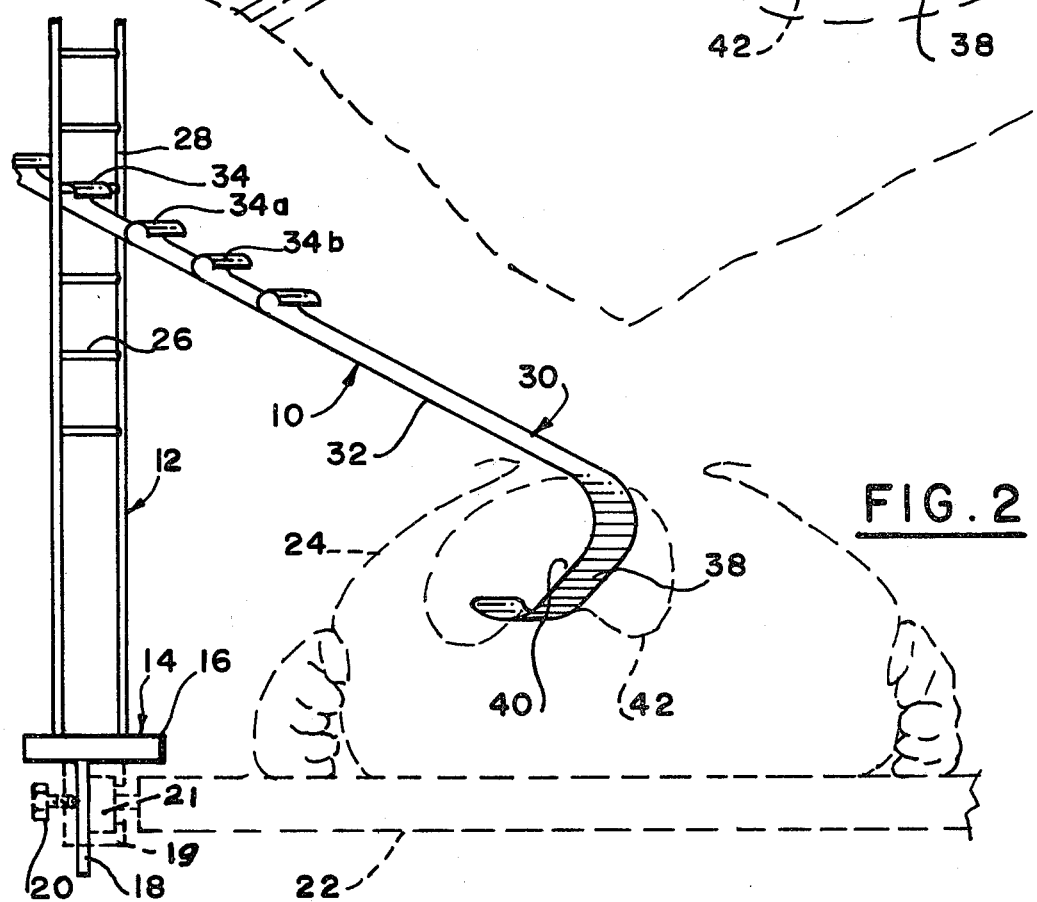
FIG. 2 is an end elevation view of the device shown in FIG. 1.

In FIG. 1 the combined liver retractor is designated by reference numeral 10 and comprises a support member 12 having a base 14 comprising a base plate 16 having a vertical attaching plate 18 which fits into a slot on a slide carrier 19 which is an open channel that is positioned and locked in place by a manually operated screw 20 which selectively engages a conventional rail 21 found on most operating tables.

The upstanding support member 12 generally resembles a small ladder having individual, spaced positions defined by transverse members 26 which resemble and are spaced apart in similar fashion corresponding to the rungs on a ladder. Rigid, spaced side members 28 are attached to the base 14 and support the individual members 26.

The retractor 30 is similar to an elongated arm and comprises a rigid strip 32 made from a suitable autoclaveable material such as stainless steel and the like and having selectively a plurality of positions defined by hooks 34 (34a, 34b, etc.) which are small curved metal plates extending across the width of the strip 32 and which are spaced from one another at intervals longitudinally along the strip 32. Each of the hooks 34 is capable of engaging and hooking one of the members 26 which is accomplished in the manner shown in FIG. 1 simply by inserting the strip 32 through the space between the side members 28 of the support 12 and pulling the strip outwardly until a particular position 34a, 34b, etc. is matched with one of the transverse members 26 which gives the elevation and angle of inclination to the strip 32 and the retractor 30.

The retractor 30 comprises a retracting end 38 which is curved to provide a gentle slope portion 40 which supports gently a portion of an organ such as the liver 42 and which is gently moved out of place. The edge of the retractor 30 is blunt to prevent laceration of the organ. It is possible for the surgeon or some other person to position the end 38 to place the liver 42 properly along the gentle slope portion 40 and then to assist in gently pulling the liver 42 back moving the retractor 30 and strip 32 through the selected space between members 26 until the proper position of the liver 42 (or other organ) has been accomplished to expose the area and open the field which is desired by the surgeon. Then the proper matching hook 34a, 34b, etc. is placed over the selected member 26. The liver 42 normally lies at an angle, following approximately the costal angle of the ribs. The tension from the retractor 30 should as closely as reasonably possible pull at that same angle. Therefore, the side members 28 and the entire support 12, although generally vertical, are in a plane at an angle to the centerline and edge of the rail 21 whereby the retractor extends at an angle across the table 22 rather than transversely straight across.

While I have shown and described a particular embodiment of my invention together with a suggested mode of operation, such as for the liver, this is by way of illustration only and does not constitute any limitation because there are various alterations, changes, deviations, eliminations, substitutions and departures which may be made in the from and mode of operation without departing from the scope of my invention as defined only by a proper interpretation of the appended claims. The device may be used to retract other organs.

What is claimed:

1. In a surgical retractor for retracting and lifting a body organ:
an elongated retractor member means for mounting on a surface such as on one side of an operating table for longitudinal adjustment upwardly or downwardly and transversely of the mounting surface to change the effective length thereof, said retractor member having opposite ends and a plurality of retaining members at spaced positions thereon,
a curved retracting end means of said retractor member means defining a slope portion in which at least part of the body organ is supported for lifting,
a support member means extending vertically upwardly to the mounting surface for adjustably supporting said retractor member above the organ on the mounting surface, whereby the height of the end of the retractor member means opposite from the slope portion may be adjusted in vertical height by moving same selectively upwardly or downwardly and substantially through said support member means to change the effective length of the elongated retractor member means, said support member means comprising a plurality of individual support members spaced from one another upwardly above the mounting surface from each other,
said retractor member means being selectively movable from one position on said support means upwardly or downwardly and selectively inwardly or outwardly relative to the mounting surface to engage a selected retaining member with one selected support member thereby to determine the height and effective length of the retractor member,
thereby to change the angle of the retractor member with respect to the transverse line of the operating table whereby the height, angle and effective length of said retractor member may be adjusted and set.

2. The device claimed in claim 1 wherein: said retaining members on said retractor member means comprise curved hook members and said spaced support members are selectively engageable with said hook members in a selected position.

3. The device claimed in claim 1 wherein: said support member means comprises a clamping means on said support member means for clamping said support member means to a stationary surface such as a table.

4. The device in claim 3 wherein said respective support member is selectively engageable with at least one of the portions on the retractor member means, said portions being fixed, open concave members.

5. The device in claim 1 wherein said retractor member is supported at an angle across said table.

6. The device in claim 1 wherein said support members are fixed, straight members selectively engaged with at least one of the portions on the retractor member means, said portions being fixed, open concave members.

7. The device claimed in claim 1, including:
said plurality of support members on said support member means comprising straight, fixed members, said positions on said retractor member means comprising open, concave fixed attaching members selectively spaced along said retractor means, whereby at least one of the vertically spaced members on the support member means selectively provides adjustment of the height, the inclination and the effective length of the retractor member means from the side of an operating table, and the open member on said retractor member means engages but does not attach or connect to said support member.

* * * * *